United States Patent
Gao

(10) Patent No.: US 7,101,671 B2
(45) Date of Patent: Sep. 5, 2006

(54) METHOD AND EQUIPMENT TO MONITOR NUCLEIC ACID HYBRIDIZATION ON A DNA CHIP USING FOUR-DIMENSIONAL PARAMETERS

(76) Inventor: Ben Gao, 1st Room 5th Floor A4 Building, Long Xiang Road, Hai Dian District, Beijing 100083 (CN)

( * ) Notice: Subject to any disclaimer, the term of this patent is extended or adjusted under 35 U.S.C. 154(b) by 503 days.

(21) Appl. No.: 10/380,112

(22) PCT Filed: Oct. 24, 2002

(86) PCT No.: PCT/CN02/00751

§ 371 (c)(1), (2), (4) Date: Mar. 11, 2003

(87) PCT Pub. No.: WO2004/038042

PCT Pub. Date: May 6, 2004

(65) Prior Publication Data

US 2004/0081974 A1   Apr. 29, 2004

(51) Int. Cl.
*C12Q 1/68* (2006.01)
*C07H 21/02* (2006.01)
*C07H 21/04* (2006.01)
*G01N 15/06* (2006.01)

(52) U.S. Cl. ................. 435/6; 536/23.1; 536/24.3; 422/68.1

(58) Field of Classification Search ............... 422/68.1; 435/6; 536/23.1, 24.3
See application file for complete search history.

(56) References Cited

U.S. PATENT DOCUMENTS 5,445,934 A    8/1995  Fodor et al.
5,744,305 A    4/1998  Fodor et al.
6,238,686 B1   5/2001  Carrino et al.
2001/0000148 A1*  4/2001  Kurane et al. ............... 435/6

FOREIGN PATENT DOCUMENTS

CN    1252453    5/2000
CN    1284568    2/2001

* cited by examiner

*Primary Examiner*—Jezia Riley
(74) *Attorney, Agent, or Firm*—Rothwell, Figg, Ernst & Manbeck, PC

(57) ABSTRACT

This invention is to provide a method for detecting DNA hybridization on DNA chips using 4-D parameters. Based on the traditional method of using 3-D parameters to detect DNA hybridization on DNA chips, this invention introduces temperature as the forth parameters to determine the melting temperatures by scanning the changes of fluorescence intensity of the fluorescent labels on the double-stranded oligo nuclei acids resulted from the increasing of hybridization temperature. Comparing the measured melting temperatures with the standard melting temperature specific for each probe on the chip is used to gain insight into the specific property of the single-stranded nucleic acids in the sample. This device is composed of a DNA chip containing transparent glass chamber, in which a temperature sensor and a thermo-circler are installed. This invention provides a specific, sensitive, and easy operating method to detect gene in a complex sample. The device used in this invention has simple structure, and can be coupled with various types of DNA chips with low cost.

11 Claims, 1 Drawing Sheet

Figure 1:
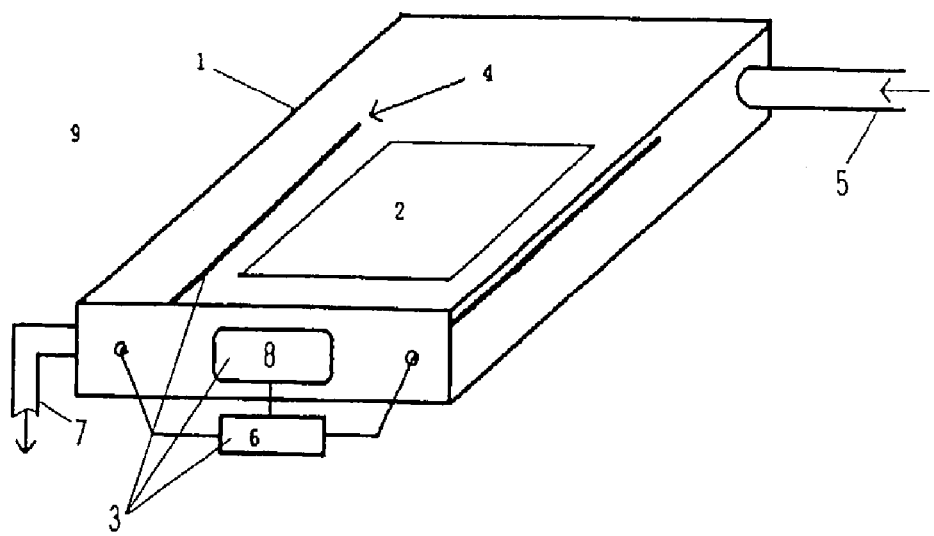

METHOD AND EQUIPMENT TO MONITOR NUCLEIC ACID HYBRIDIZATION ON A DNA CHIP USING FOUR-DIMENSIONAL PARAMETERS

FIELD OF THE INVENTION

This invention is about gene detection technologies emphasized on the specific methods and equipments to monitor nucleic acid hybridization on a DNA chip using four-dimensionalparameters.

BACKGROUND OF THE INVENTION

In 1953, Watson and Crick suggested the concept of double stranded DNA. They had some significant discoveries. (1) DNA molecules were composed of two anti-parallel poly-nucleic acid chains. (2) There were rules for paring the four bases—chargaff et al. analyzed the base compositions of DNA molecules by chromatograph from many organisms, and found that the numbers of A and T were equal, while the numbers of C and G were also equal. So they suggest there exist four possible base pairs: A-T, T-A, G-C and C-G. (3) The connection of the two chains were through hydrogen bounds—the surface of the base pairs goes through and was roughly perpendicular to the axis. Two and three hydrogen bounds can form between the A-T and G-C pairs, respectively. Meanwhile, hydrophobic force also contributes to stabilize the DNA double helixes. (4) Because all the base pairs follow these rules, every chain can have random sequences. However, once the sequence of one of the chains is determined, the other one must have the corresponding nucleotide sequences.

As the DNA double helix is maintained by both hydrogen bound and hydrophobic force, factors, such as heat, pH, organic solvent, etc., which can destroy hydrogen and hydrophobic bounds, would denature DNA double helixes to random single chain threads. The annealing between denatured DNA single chains through pairing is called hybridization. Hybridization can occur between homologous DNA molecules as well as homologous DNA and RNA molecules. During hybridization, the two complementary single-stranded DNA chains form double-stranded hybrids through non-covalent bounds. When the sequence of one of the chains is known, the existence of its complementary chain in an unknown DNA sample can be detected through hybridization.

Based on the above principle, many gene products have been developed, among which gene sensor has many applications.

Recently, the research in the field of DNA sensor (DNA or nucleic acid sensor) has become the hot spot of research. Gene sensor, as a simple, fast, and cheap detection method, has many potential applications in the fields of molecular biology, medical analysis, and environment monitoring. It can also be applied to study DNA-drug and protein-protein interactions in addition to sequence analysis, mutation detection, gene detection, and clinical diagnostics.

The method for gene analysis to analyze DNA sequences in non-homogenous system is now through DNA hybridization. Hybridization can occur between homologous DNA molecules as well as homologous DNA and RNA molecules. During hybridization, the two complementary single-stranded DNA chains form double-stranded hybrids through non-covalent bounds. When the sequence of one of the chains is known, the existence of its complementary chain in an unknown DNA sample can be detected through hybridization. The most common method is to fix a single DNA chain with known sequence information on a solid surface, and use it to hybridize to the complementary single chains in the sample buffer to detect the existence of the wanted DNA molecule in the liquid phase.

Recently, such research is getting deeper and deeper, and there is great value in DNA detection through hybridization. The major applications rely in the fields of clinical diagnostics, forensic science, food industry, biochemistry, environment protection, etc. The application of using non-radioactive labels such as biotin, digosin, and fluorescent dyes has made the detection more convenient and safer. In particular, the application of PCR amplification has made the method very sensitive.

The traditional DNA hybridization reaction requires a labeling step to detect hybridization signals, which allow in situ detection, and can achieve high sensitivity. For example, PCR technology can reach the detection limit at the nmol/l range. Bioinformatics also provides means to detect a specific DNA sequence from a complex mixture of DNA. Because of using short wave fluorescence and co-focal microscopy, fluorescent labeling has become the routine method for detecting nano-amount of DNA molecules. Among the available fluorescent labeling methods, the device of DNA chip (gene chip or DNA microarray) only include the XYZ three-dimensional (3-D) parameters, such as the Affymetrix GeneChip. On these chips oligo nucleic probes are fix on glass surface, and their base composition and chain length can be represented by XYZ 3-D parameters. The single-stranded oligo target sequences are directly labeled with fluorescent dyes, hybridized to the probes on the chip to form double helixes, followed by the detection by using a scanner to obtain sample information. The U.S. Pat. No. 5,445,934 and U.S. Pat. No. 5,744,305, disclosed the technologies and device of using photolithography to fabricate high-density DNA probes on a DNA chip. In such device the hybridization between all the fixed probes on the chips and the other DNA molecules in the sample buffer was carried out at the same temperature. Because of the differences between the probe lengths, base composition (GC content), the Tm (melting temperature), which represents the temperature when 50% of the probes and their targets are separated, are different. Therefore, the optimum hybridization temperatures are different for each probe. Because of such discrepancy in hybridization temperature, the accuracy of results cannot be guaranteed, and single base mismatch cannot be detected. To overcome such disadvantages, U.S. Pat. No. 6,238,868 described a type of microarrays by introducing electric filed as a free parameter to expedite the hybridization procedure. However, this technology is complicated, high cost, and requires the labeling of oligo target sequences or hybridizing with another reporter probes with fluorescent dyes. As a result it cannot guarantee the accuracy of results, and limited the application of hybridization microarrays.

Recently, some researchers begin to use non-labeling methods to analyze gene sequences. The most popular one is the DNA biosensor system. These biosensors can be categorized into three classes: (1) optical biosensor, which can be further divided into three classes of fluorescent optical fiber gene sensor, surface enhance Raman gene probe and surface plasmon resonance gene sensor, (2) electro-chemistry biosensor, and (3) piezo gene biosensor. Further information of their specificity and sensitivity is still waiting.

DETAILED DESCRIPTION OF THE INVENTION

The purpose of this invention is to provide a method for detecting DNA hybridization on DNA chips using 4-D parameters. Based on the traditional method of using 3-D parameters to detect DNA hybridization on DNA chips, this invention introduces temperature as the fourth parameters to determine the melting temperatures by scanning the changes of fluorescence intensity of the fluorescent labels on the double-stranded oligo nuclei acid resulted from the increasing of hybridization temperature. This method is simple, accurate, sensitive and specific.

Another purpose of this invention is to provide a device for detecting DNA hybridization on DNA chips using 4-D parameters. This device is simple, low cost, and can guarantee the accuracy of results from high-density microarrays even with the discrepancy in hybridization temperature.

This invention is achieved through the following methods:

Method to monitor nucleic acid hybridization on a DNA chip using four-dimensional parameters includes the following steps:

(1) Place the DNA chip in a temperature-controlled chamber;

(2) Incubate the chip with the single-stranded target oligos and the double-stranded chains inserted with the fluorescent dye in a reaction buffer, lower the temperature to the annealing temperature (Th) to allow for the hybridization between the probes on the chip and the single-stranded targets, which results the labeling of the double helixes with the fluorescent dye;

(3) Increase the temperature in the device from Th to 100° C. at the speed of 0.001–1° C./sec, during which at each $\Delta T°$ C. (defined as the temperature difference per second of increasing) the chip was scanned by a scanner to obtain the fluorescent intensity F; When the temperature in the device reaches the melting temperature Tm, the double strands disassociate, the fluorescent dye diffuses into the buffer, resulting in a rapid loss of fluorescent intensity; The scanning of fluorescent intensity of every probe on the chip records the turning point on a continuous melting curve of the double-stranded DNA, or on a derivative curve, which must provide the Tm of the double-stranded molecules at the peak position on the curves; By comparing the above Tm with the calculated Tm of known sequences, the property of the oligo single chain that hybridizes with the surface probes can be obtained.

In preferred embodiments, to wash off the excess target oligo chains and reaction buffer, a washing step at annealing temperature with buffer free of fluorescent dyes was also included in the above item (2).

The preferred conditions are as follows:

Annealing temperature Th is at 4–89° C.;
Melting temperature Tm is at 8–100° C.;
Speed of temperature increasing is 0.01–1° C./sec.

The above reaction buffer of fluorescent dye is one of the SYBR Green I, SYBR Green II, and SYBR Gold buffers (Molecular Probe, USA).

Another purpose of this invention can be achieved using the following steps:

Device to monitor nucleic acid hybridization on a DNA chip using four-dimensional parameters includes the container for DNA chips, DNA chips, temperature controlled thermocycler, and the buffer input and output; The DNA chips are placed in the chip container, which is connected to the thermocycler.

The above temperature controlled thermocycler is composed of temperature sensor, thermocycler and temperature controlling devices; of these, the temperature sensor is connected to the temperature controlling device which is also connected to the thermocycler.

This invention further provides practical applications of using the device for monitoring nucleic acid hybridization on a DNA chip using four-dimensional parameters.

The device to monitor nucleic acid hybridization on a DNA chip using four-dimensional parameters can also be used to analyze and separate DNA samples.

The device to monitor nucleic acid hybridization on a DNA chip using four-dimensional parameters can also be used to analyze and separate RNA samples.

This invention has the following advantages over the existing technologies:

1. Based on the traditional method of using 3-D parameters to detect DNA hybridization on DNA chips, this invention introduces temperature as the fourth parameters to determine the melting temperatures by scanning the changes of fluorescence intensity of the fluorescent labels on the double-stranded oligo nuclei acids resulted from the increasing of hybridization temperature. This method is simple, accurate, sensitive and specific.

2. This invention introduces the temperature scanning method to solve the problem whether the results are accurate caused by the discrepancy in hybridization temperature, and provides simple and definitive yes/no answers to the results.

3. The target oligo sequences used in this invention does not require a labeling step nor another fluorescence-labeled reporter probe, which simplified the operation.

4. The device in this invention has simple structure, and can be coupled with various commercially available chips to reduce the cost; Even with differences in hybridization temperatures, this invention still guarantees the accuracy of results from high-density microarray assays.

DETAILED DESCRIPTION OF THE FIGURES

FIG. 1. The structure of the device of this invention.

Figure 2A:
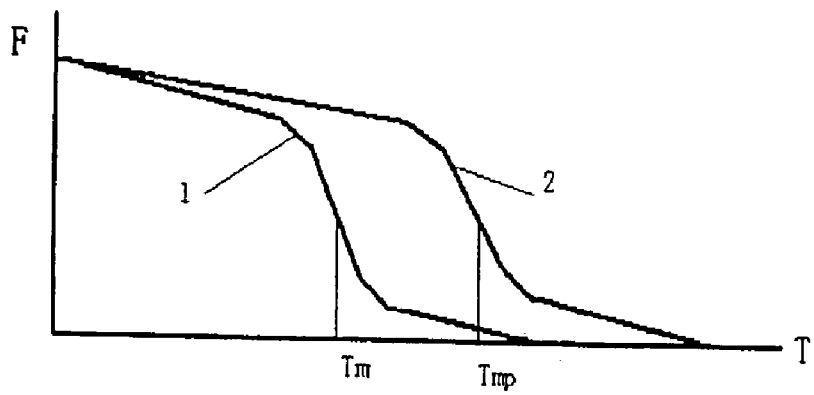

FIG. 2A. The melting temperature curves (F~T) obtained by scanning the DNA chips using the device of this invention.

Figure 2B:
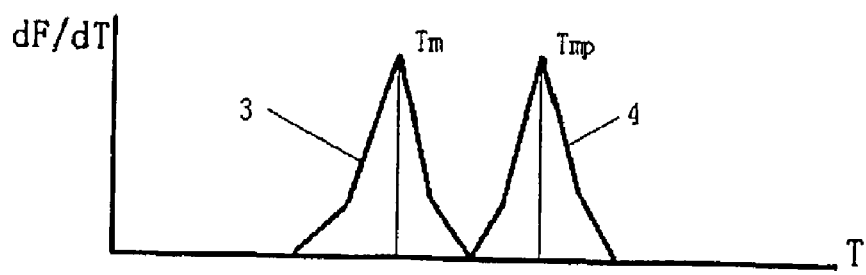

FIG. 2B. The derivative melting temperature curves (F~T) obtained by scanning the DNA chips using the device of this invention.

DESCRIPTION OF PREFERRED EMBODIMENT

FIG. 1 describes the device to monitor nucleic acid hybridization on a DNA chip using four-dimensional parameters. As shown in the figure, Device 9 includes a transparent glass box 1, a commercially available DNA chip 2, a Temperature Controlled Thermocycler Device 3, a buffer input 5 and buffer output 7. The Temperature Controlled Thermocycler Device 3 includes a Temperature Sensor 4, a Thermocycler 8 and a Temperature Controlling Device 6. The Temperature Controlling Device 6 is a temperature controlling computer. Device 4 and Device 6 are connected, and Device 6 and Device 8 are also connected. The temperature controlling computer 6 is programmed to control the temperature of the buffer and DNA chips 2 in the glass chamber 1 through the Temperature Sensor 4 and the Thermocycler Device 8.

Based on this invention, the single-stranded target oligos and the double-stranded chains inserted with the fluorescent dye are mixed in a hybridization buffer and added to the glass reaction chamber 1. The temperature in chamber 1 is rapidly lowered to the annealing temperature (Th=4~89° C.), and chamber is washed with phosphate buffer to remove the excess oligos and reaction buffer. Use thermocycler 8 to increase the temperature in chamber 1 from Th to 100° C. at the speed of 0.01° C./sec, during which at each 0.01° C. increase the chip 2 was scanned by a scanner to obtain the fluorescent intensity F. As long as the Th is low enough, single-stranded oligos in the sample will form the double helixes with the probes on the chip, resulting in the insertion of high concentration of SYBR Green I dye into the double-stranded oligos. Excited by laser at 470–490 nm, the dye will emit specific fluorescence at the wave length of 530 nm. With the temperature increasing to the melting temperature Tm (Tm=8–100° C.), double-stranded oligos melt to release the single-chained target oligos from the corresponding probes on the chip 2, which leads to the diffusion of SYBR Green I into the buffer that causes the rapid loss of fluorescent signals. The turning points on the melting temperature curves (F~T) (FIG. 2A) or the derivative melting curve (dF/dT~T)(FIG. 2B) obtained by scanning the DNA chips will define the melting temperature Tm. In FIG. 2A, F represents the fluorescent intensity of the probe, T represents temperature, Curve 1 is the melting curve of a double helix with mismatch, and Curve 2 represent the melting curve of a perfect match. In FIG. 2B, dF/dT is the derivative of fluorescent intensity to temperature, where T represents the temperature; Curve 3 is the melting curve of a double helix with mismatches; Tm represents the temperature at the peak of the curve, namely the melting temperature; Curve 4 represent the melting curve of a perfect match. Tmp, namely the melting temperature, which is at the peak position of the curve, also represents the specific melting temperature of the probe. Tmp can be obtained using the standard samples with perfect matches to the probe. When Tm is less than Tmp, we can conclude that there exist mismatches between the target oligos and the probe, because their binding force is less than that with perfect matches. Only when Tm is equal to Tmp can one tell that the pairing is perfect.

INDUSTRIAL APPLICATIONS

This invention can be used to detect whether specific DNA sequences are present in the nucleic acid samples:

By heating the double-stranded sample nucleic acids to >94° C., the DNA molecules will denature to single-stranded chains (or through other means to obtain single-stranded DNA). The resulting single-stranded DNA and reaction buffer are then flowed into the device described in this invention. Using temperature scanning methods, the melting temperatures Tm of every pair of the target and probes on the chip can be determined. If the target and probe are perfect match, the binding force between the two chains are maximum, resulting in the maximum Tm, which is equal to the specific Tmp of the probe. If one (or more than two) mismatch exists between the target and the probe, the binding force will be less, and the corresponding melting temperature Tm will be lower than the Tmp. In other words, the standard to judge whether the result is reliable is to compare the Tm with the specific Tmp of each probe. Therefore, this method will tell whether the corresponding target oligos to the probes on the chip exist in the sample nucleic acids.

This invention can also be used to separate different DNA molecules in the sample:

Incubate single-stranded target DNA and the reaction buffer in the chamber described in this invention, and only select for the chip containing probes with a single Tmp. Temperature scanning is then used to monitor the Tm of the target and probe oligos at various spots on the chip. Disregard the washing buffer when the Tm is less than Tmp. Therefore, the buffer eluted at or greater than the specific Tmp should contain those target DNA molecules with perfect matches to the probes on the chip robes on the chip.

The invention claimed is:

1. Method for detecting DNA hybridization on DNA chips using 4-Dimensional parameters which comprises the following steps:
    (1) placing a DNA chip containing probes in a temperature-controlled chamber;
    (2) incubating the DNA chip with single-stranded target oligos and a fluorescent dye in a reaction buffer, wherein the fluorescent dye inserts into double-stranded DNA molecules;
    (3) lowering the temperature in the temperature-controlled chamber to the annealing temperature (Th), wherein the single-stranded target oligos hybridize to the probes on the chip to form double-stranded DNA molecules and wherein the fluorescent dye inserts into the double-stranded DNA molecules thereby, labeling the double-stranded DNA molecules with the fluorescent dye;
    (4) increasing the temperature in the temperature-controlled chamber from Th to 100° C. at the speed of 0.001–1° C./sec,
    (5) scanning the chip at each $\Delta T°$ C. by a scanner to obtain a fluorescent intensity F, wherein when the temperature in the termparature-controlled chamber reaches the melting temperature Tm for a given probe, the double-stranded DNA molecule dissociates and the fluorescent dye diffuses into the buffer, resulting in a rapid loss of fluorescent intensity; wherein the scanning of fluorescent intensity of every probe on the chip records the turning point on a continuous melting curve or a derivative melting curve for each of the double-stranded DNA molecules, which provides the Tm of each of the double-stranded DNA molecules at the peak position on the curves; and
    (6) comparing the Tm for each probe from step (5) with the known optimum melting temperature for each of probe that hybridizes perfectly with a complementary target oligo (Tmp) to detect the presence of the perfectly complementary target oligo, wherein the target oligo is present when the Tm equals Tmp for a given probe.

2. The method of claim 1, which further comprises washing the DNA chip at the annealing temperature to wash off the excess target oligos, fluorescent dye and reaction buffer.

3. The method of claim 1, wherein the annealing temperature Th is in the range of 4–89° C.

4. The method of claim 1, wherein the melting temperature Tm is in the range of 8–100° C.

5. The method of claim 1, wherein the temperature increasing speed is at 0.01–1° C./sec.

6. The method of claim 1, wherein the fluorescent dye is SYBR Green I, SYBR Green II, or SYBR Gold.

7. A device adapted for performing the method of claim 1 comprising a transparent glass box, a temperature controlled themocycler device connected to the glass box, and a buffer input and a buffer output connected to the glass box.

8. The device of claim 7, wherein the Temperature Controlled thermocycler device comprises a Temperature Sensor, a a thermocycler and a Temperature Controlling Device;

the temperature sensor and the temperature controlling device are connected, and the temperature controlling device and the thermocycler are also connected.

9. The device of claim 7 for analyzing and separating DNA samples.

10. The device of claim 7 for analyzing and separating RNA samples.

11. The device of claim 7 which further comprises DNA chips.

* * * * *